United States Patent [19]
Lambert et al.

[11] Patent Number: 5,626,749
[45] Date of Patent: May 6, 1997

[54] APPARATUS FOR CENTRIFUGING OF A LIQUID PACKAGED IN FLEXIBLE-WALLED BAGS CONNECTED TO AT LEAST ONE FILTER

[75] Inventors: Roland J. L. R. Lambert, Reze; Jean-Claude C. M. Letourneur, Pornichet, both of France

[73] Assignee: Jouan (societe anonyme), Saint-Nazaire, France

[21] Appl. No.: 345,437

[22] Filed: Nov. 21, 1994

[30] Foreign Application Priority Data

Nov. 23, 1993 [FR] France .................... 93 14003

[51] Int. Cl.⁶ .................... B01D 21/26; B01D 35/02
[52] U.S. Cl. .................... 210/257.1; 210/435; 210/782; 604/410; 436/177; 494/36; 494/45
[58] Field of Search .................... 210/232, 257, 210/206, 435, 477, 483, 484, 782, 787; 604/406, 408, 409, 410; 436/177; 494/36, 45

[56] References Cited

U.S. PATENT DOCUMENTS

| 4,439,177 | 3/1984 | Conway . |
| 5,100,564 | 3/1992 | Pall . |
| 5,456,845 | 10/1995 | Nishimura et al. ............ 210/782 |

FOREIGN PATENT DOCUMENTS

| 0499891 | 8/1992 | European Pat. Off. . |
| 0591980A2 | 4/1994 | European Pat. Off. . |

*Primary Examiner*—David A. Reifsnyder
*Attorney, Agent, or Firm*—Larson & Taylor

[57] ABSTRACT

Method of treatment by centrifuging of a liquid packaged in flexible-walled bags connected to at least one filter. According to the method, the filter (2) is placed in the middle of the confinement space (5, 5a) such that the large faces of the filter (2) are parallel to the centrifuging axis (3), and bags (1) are placed on either side of said filter (2) so that they are in contact with the latter.

9 Claims, 3 Drawing Sheets

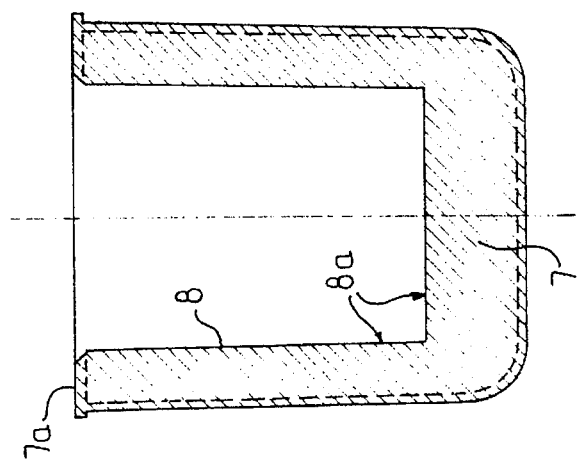
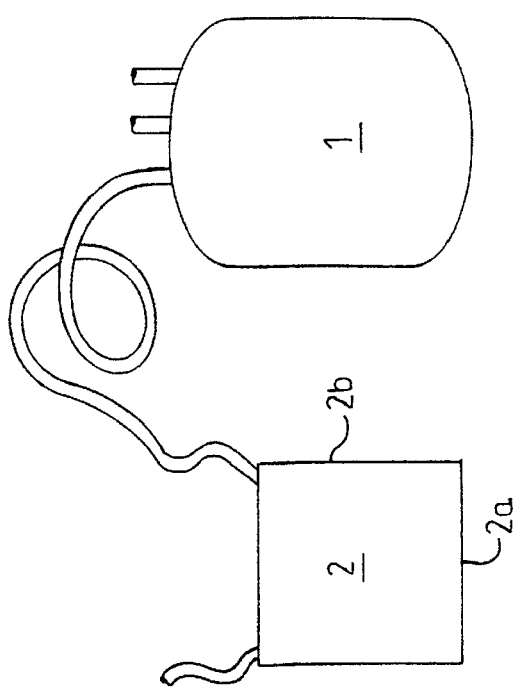
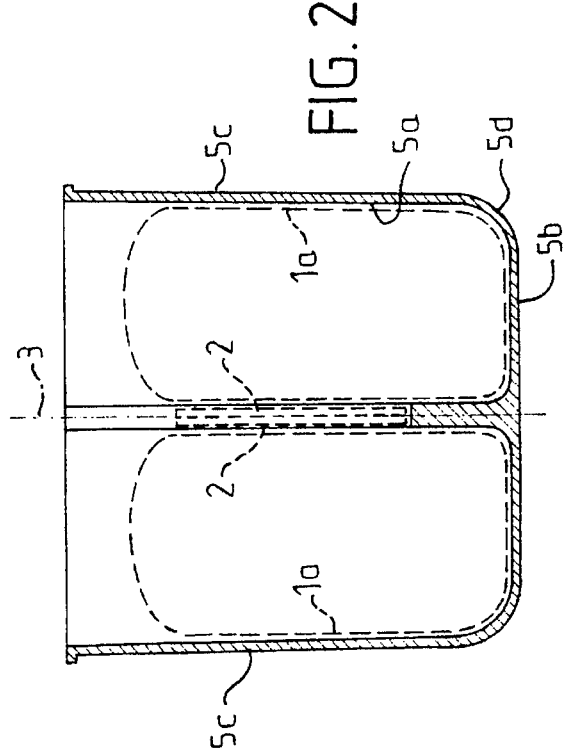
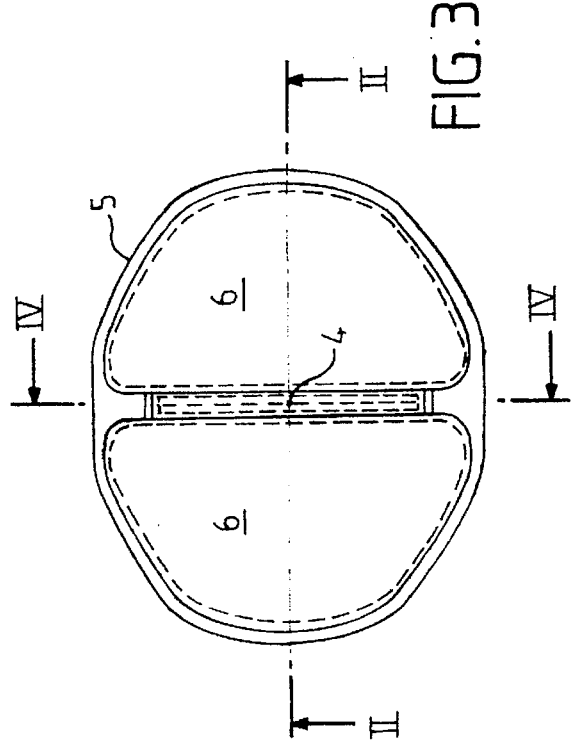

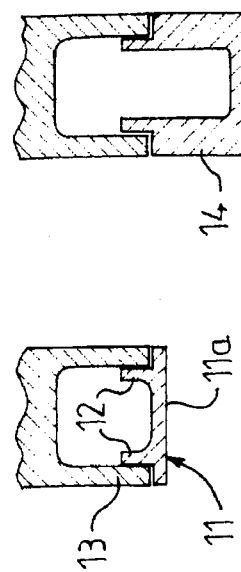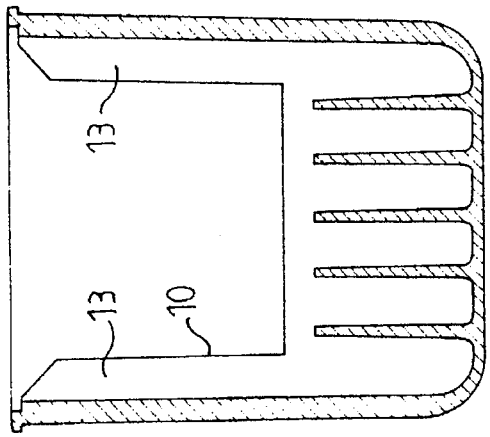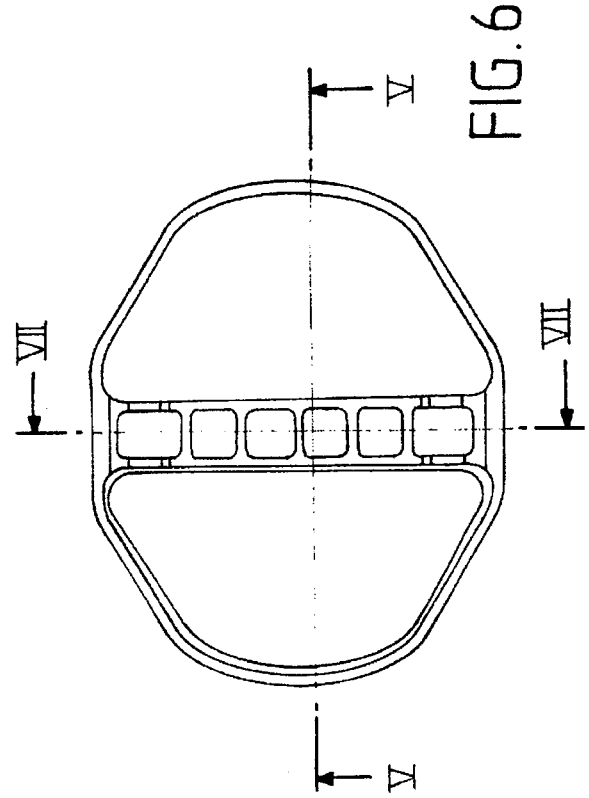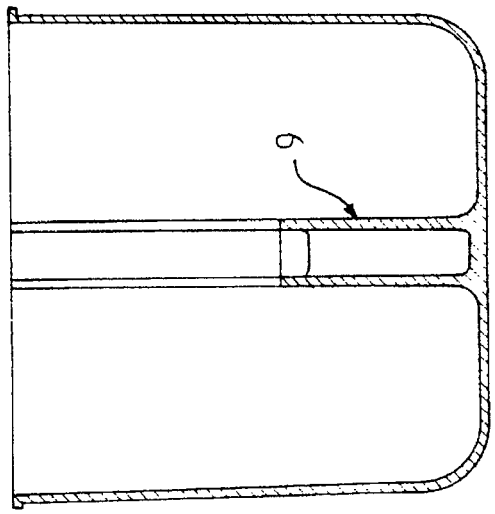

APPARATUS FOR CENTRIFUGING OF A LIQUID PACKAGED IN FLEXIBLE-WALLED BAGS CONNECTED TO AT LEAST ONE FILTER

The present invention relates to the centrifuging of liquid with a view to preparing products such as blood components, which preparation requires, after centrifuging the liquid, filtration of the centrifuged product in order to separate the constituents thereof.

The invention more particularly relates to the centrifuging of assemblies formed by at least one flexible-walled bag connected to a filter via a flexible tube.

In methods for preparing blood products, the starting product, blood, is transferred then centrifuged and finally filtered in order to separate the constituents thereof, it being necessary for these operations to be carried out under strict sterility conditions. The starting product is therefore, before centrifuging, packaged in flexible-walled bags connected together by flexible tubes with, however, a filter occasionally included in the circuit. This filter generally consists of a rigid casing of flat shape, the internal volume of which is separated into two parts by a filtering wall.

Since the filters and the bags need to remain connected in order to prevent any risk of contamination, there is therefore no other choice than to place the assembly formed by the bags and the filters which are connected to them in a centrifuge enclosure.

This operation of centrifuging bags and filters in one and the same enclosure, that is to say in the same confinement space, has the following difficulties:

Since the filters are of flat shape and include an internal volume containing only gas and a filtering wall, they are vulnerable not only with respect to the centrifugal forces developed on their walls but also with respect to the pressures exerted by the neighboring bags on their walls during centrifuging.

The pressure existing in the liquid contained in bags subjected to centrifuging typically reaches several kilograms, or even several tens of kilograms per square centimeter, which makes the bags themselves extremely fragile with respect to the action which solid bodies, centrifuged at the same time as them and being in contact with them, might have on them. In principle, if these solid bodies have a shape which is not compact and comprises edges, like the abovementioned filters, the danger of the bags being damaged or even bursting is considerable.

The invention overcomes these drawbacks and its object is in particular to provide a method making it possible to centrifuge, simultaneously and in one and the same confinement space, bags and at least one filter, and which minimizes the risk of damage to these elements.

For a method consisting in confining assemblies comprising bags and at least one filter in a confinement space of defined shape which is rotated at high speed about a defined axis passing through the middle of said space, this object is achieved, according to the invention, by virtue of the fact that the filter is placed in the middle of the confinement space such that the large faces of the filter are parallel to the centrifuging axis and by virtue of the fact that the bags or assemblies of bags are positioned on either side of said filter.

Advantageously, during the centrifuging, the lower edge and the side edges of the filter are positively held in constant positions with respect to the confinement space.

Advantageously, the bags are first positioned in the confinement space, then the filter is placed between the bags such that each of its large faces are in contact with one bag.

In the case in which an assembly comprising several filters is treated, these filters are placed in the middle of the confinement space, stacked on one another via their large faces, and the bags are placed on either side of said stack.

The invention also relates to a device for centrifuging assemblies comprising flexible-walled bags filled with liquid and at least one filter connected to said bags. This device includes a centrifuging support in the form of a container which is open upward, having a vertical central axis and capable of being driven in rotation at a suitable speed about said axis, the support constituting, via its internal walls, said confinement space.

In this device, according to the invention, the support includes means for supporting and positioning at least one filter and for constituting with the latter a vertical partition of plane general shape, passed through substantially in its mid-plane by said central axis and subdividing the internal volume of the support into two compartments intended to contain the bags.

Advantageously, the filter supporting and positioning means include means providing a housing for at least one filter, this housing being bounded downward and laterally by a surface whose contour substantially matches the shape of that of the filter.

By virtue of this feature, the housing means receive the filter substantially without play parallel to its plane, so that said contour of the housing constitutes a means positively holding the lower and side edges of the filter in a constant position of the confinement space.

The support and positioning means consist, for example, of a solid partition with substantially parallel faces. In this case, the housing means advantageously consist of a single opening which is made in said wall starting from its upper edge and whose contour substantially matches the shape of that of a filter.

According to another embodiment of the invention, the housing means comprise an insert in the shape of a stirrup, which is removably mounted in the support, which is capable of receiving at least one filter in its opening and whose internal surface has a contour substantially matching the shape of that of the filter.

It is advantageous for the centrifuging support to have a horizontal section of elongate shape and for said partition to extend along the small dimension of this horizontal section.

According to a preferred embodiment, each compartment is shaped and dimensioned so that a single bag or a single bag assembly arranged in said compartment is in contact with all of the walls of the latter, including said partition, which the support and positioning means with the filter constitute.

The advantages of the invention defined herein-above are manifold:

It makes it possible to position the filters at a location and in a position such that they do not risk damaging the bags.

It makes it possible to position the filters at a location where the centrifugal force has the lowest value possible, which limits the effect of pressure on these filters.

It makes it possible to hold the filters in a constant location and position which are therefore predefined, with respect to the confinement space constituted by the internal walls of the support. It is thus possible to test the strength of the filters with respect to the centrifugal forces beforehand, before connecting them to bags which will subsequently be filled with blood to be treated.

Further advantages and features will emerge on reading the description which follows of several embodiments of the invention, which description is made with reference to the attached drawings, in which:

FIG. 1 is a diagrammatic plan view of an assembly composed of a bag and a filter;

FIG. 2 is a view in elevation and in vertical section along the plane II—II in FIG. 3, of a centrifuging support according to a first embodiment of the invention;

FIG. 3 is the plan view corresponding to FIG. 2;

FIG. 4 is a view in elevation and in vertical section along the plane IV—IV in FIG. 3, of the support represented in FIGS. 2 and 3;

FIG. 5 is a view in elevation and in vertical section along the plane V—V in FIG. 6, of a centrifuging support according to a second embodiment of the invention;

FIG. 6 is the plan view corresponding to FIG. 5;

FIG. 7 is a view in elevation and in vertical section along the plane VII—VII in FIG. 6, of the support represented in FIGS. 5 and 6;

FIG. 9 represents the fitting of the insert, seen in section along the plane IX—IX in FIG. 8, in the notch of the wall means of the support represented in FIGS. 5 to 7; and FIG. 10 is a similar view to FIG. 9, showing an insert of a different size suited for filters of smaller dimensions.

FIG. 1 shows an assembly used in methods for preparing blood components. The blood is transfused into flexible-walled bags such as the bag 1 which are already connected together by flexible tubes and already include a flat filter 2 of rectangular shape in the circuit, which filter is composed of a rigid casing whose internal volume is separated into two parts by a filtering wall.

Figure 8:
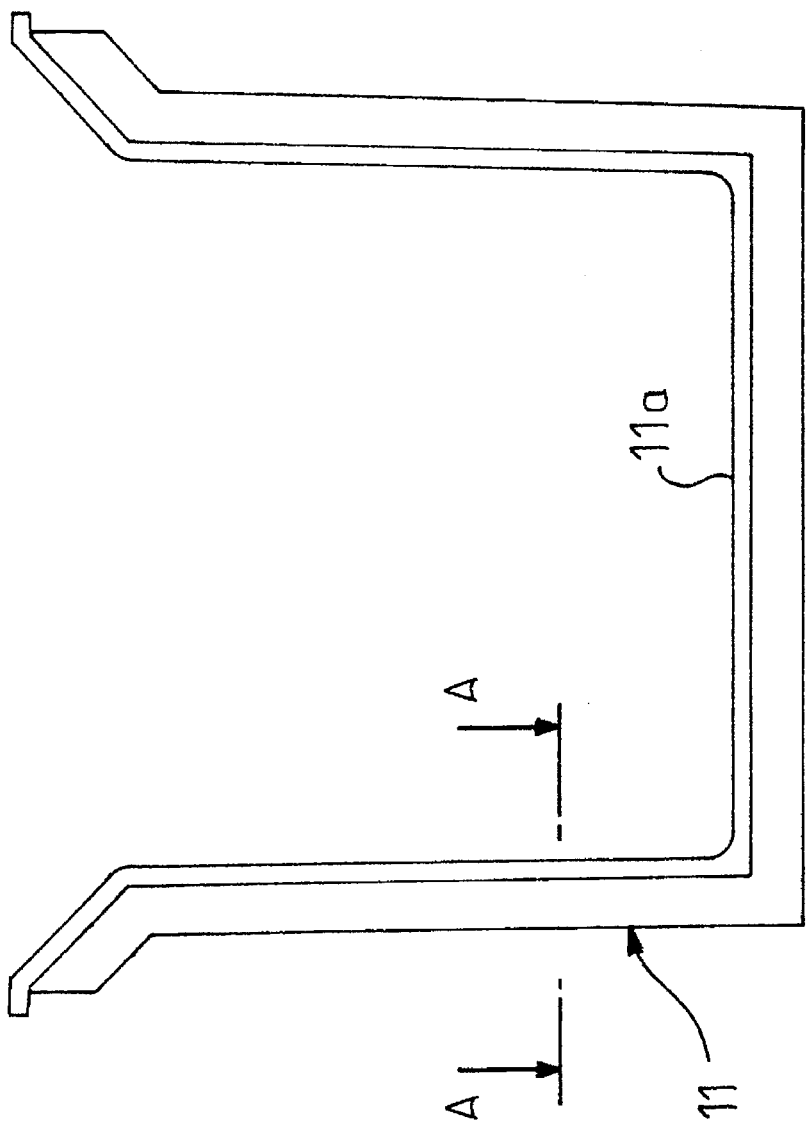
FIG. 8 is a view in elevation of an insert intended to be mounted on the support represented in FIGS. 5 to 7.

The assembly formed by the bags 1 and the filter 2 is to be centrifuged in order to separate the constituents of the biological liquid, then these constituents are isolated from one another by a subsequent filtering operation carried out by means of the filter 2 of the circuit.

As can be seen in FIGS. 2 and 3, during the centrifuging, the filters 2 are positioned vertically, aligned and stacked on one another via their large faces, such that said large faces of the! filters are parallel to the centrifuging axis 3 (FIG. 2), and that said centrifuging axis 3 passes through said stack of filters 2 substantially through the center 4 of its cross section (FIG. 3).

In addition, as can be seen in FIGS. 2 and 3, during the centrifuging, assemblies 1a of bags 1 (assemblies represented in dotted lines in FIGS. 2 and 3) are positioned on either side of said stack of filters 2, and the lower edge—or face—2a and the side edges—or faces—2b of the filters are positively held in constant positions with respect to the confinement space which is constituted by the internal surface 5a of the walls of a centrifuging support—or holder—5 in the form of a container which is open upward and has generally ovoid horizontal section.

The central axis of the holder 5, that is to say the axis joining the centers of its horizontal sections, coincides with the centrifuging axis 3.

The bottom wall 5b of the holder is connected to the side walls 5c by gentle curves 5d in order to match the natural shape of the liquid-filled bags 1.

The holder 5 is, for example, made of plastic. It is intended to be mounted in a metal centrifuging bucket.

In addition, as can be seen in FIGS. 2 and 3, during centrifuging, the stack of filters 2 is positioned such that the free large face of each end filter of the stack is in contact with the adjacent bag(s) 1 of said bag assemblies 1a.

Two bag assemblies 1a are placed in one and the same holder 5, each at one end ore the oval of the holder 5, on either side of the stack of filters 2.

A vertical partition of plane general shape extends radially in the direction of the minor axis of the holder 5, through which partition the centrifuging axis 3 passes substantially in its mid-plane. This partition subdivides the internal volume of the holder 5 into two compartments 6 which are symmetrical with one another with respect to the mid-plane of the partition, which plane coincides with the section plane IV—IV in FIG. 3.

According to a preferred embodiment, each compartment 6 is shaped and is dimensioned so that a single bag 1 arranged in the latter is in contact with all of the walls of said compartment, including the partition.

This partition consists of the stack of filters 2 housed in a housing made in support and positioning means which will be described in detail hereinbelow.

According to the embodiment represented in FIGS. 2 to 4, the means for supporting and positioning the filters consist of a single solid partition with substantially parallel faces 7, which is solidly attached to the holder 5, for example integrally molded with the latter. The housing means consist of a rectangular opening (or notch) 8 made in the partition 7 starting from the upper edge 7a of the latter, this opening receiving the stack of filters 2.

The contour 8a of the opening 8 substantially matches the shape of that of a filter 2, so that the filters 2 are housed therein practically without play parallel to their large faces.

The result of this is that: the contour 8a of said opening 8 constitutes a means for positively holding the lower edge 2a and side edges 2b of the filters in a constant position of the confinement space, when the assemblies 1, 2 are centrifuged and that the stack of filters 2 is clamped by the bag assemblies 1a located on either side of this stack.

According to the embodiment represented in FIGS. 5 to 7, the means for supporting and positioning the filters consist of an internally partitioned hollow wall 9 solidly attached to the holder 5, which wall also includes an opening 10 of rectangular shape made starting from the upper edge of said partition 9. However, this embodiment differs from the preceding one in that the means for housing the filters 2 are here constituted by a removable insert 11 in the general shape of a stirrup (FIG. 8) which is capable of being slid into the opening 10 until it abuts against the horizontal lower edge 10a of the latter. The insert 11 is held in position with respect to the wall 9 by virtue of the interaction of peripheral ribs 12 forming a guide element which engage, with sliding play, in a slide rail formed by ribs 13 of the wall 9, which ribs extend toward the inside of the opening 10 and over the length of the vertical side edges of the latter. The ribs 12 and 13 thus constitute means for removably mounting the insert 11 on the partition 9.

The internal surface 11a of the stirrup-piece 11 is shaped and dimensioned so as substantially to match the shape of the rectangular perimeter of a filter 2.

The embodiment of the holder having an insert has the advantage, over that of the holder without an insert represented in FIGS. 2 to 4, that one and the same holder can be used successively for filters with different shapes and/or sizes: it is sufficient for this purpose to change the insert. FIG. 10 shows the cross section of an insert 14 whose opening has smaller dimensions. The internal surface 14a of the insert 14 matches the contour of a filter having smaller dimensions than that which is suited to the insert 11 in FIG. 9.

The holders which have just been described are advantageously used in the following manner:

The filters 2 are placed vertically in the opening 8 of the partition 7 or in the insert 11 mounted in the partition 9, after the flexible bags 1 have been placed in their respective housings 6. There is therefore no wall separating the filters 2 from the bags 1. The filters 2 are held in this position by the pressure which the bags 1 exert on them. Since the centrifugal force increases during the centrifuging operation, the filters 2 remain in their initial position.

No space is therefore wasted since there is no wall separating the filters 2 from the bags 1. A holder is thus obtained whose dimensions are as small as possible.

Because the housing (opening 8 of the partition 7, or the stirrup-piece 11) intended to receive the filters 2 exhibits, in its periphery, the shape of the filter 2, the latter, during centrifuging, rests on the largest possible surface area, thus reducing to a minimum the force sustained by the filter and developed by the centrifugal force.

This force is further minimized by the fact that the depth of this housing (thickness of the opening 8 or of the stirrup-piece 11) is chosen to be as small as possible.

In this way, by virtue of the invention, the pressure exerted by the bags 1 on the filters 2 and the thrust of the centrifugal force on the filters 2 themselves are minimized.

Finally, the situation of this housing for a filter, which is of plane general shape, remains compatible with the shape which the liquid-filled bags 1 may adopt under the effect of the centrifugal force.

For the user, the actual shape of the holder, with its opening 8 or 10, prevents any ambiguity as to the location where the filters 2 should be placed. This produces a significant reduction in the risk of breakage of the filters or piercing of the bags by the filters, which constitute a major risk of environmental contamination.

We claim:

1. A device for treatment by centrifuging of a liquid package in a plurality of flexible-walled bags which are connected via a flexible tube to at least one filter of substantially flat shape with opposite faces, according to which the bags are placed, with the filter, in a confinement space which is rotated about a central rotation axis passing through said space, wherein said at least one filter is placed in said faces of said at least one filter parallel to said central rotation axis, and said bags are respectively placed on said opposite faces of said at least one filter in said device and including a centrifuging support container having an open side constructed and arranged to be driven in rotation at high speed about said central rotation axis, and which defines said confinement space, wherein the support includes means for supporting and positioning at least one filter and for constituting with the latter a partition of plane general shape, passed through substantially in its mid-plane by said central rotation axis and subdividing the internal volume of the support into two compartments constructed and arranged to contain said bags.

2. The device as claimed in claim 1, wherein the support and positioning means include housing means for at least one filter, which comprises a lower and two lateral surfaces whose contour substantially matches the shape of said at least one filter.

3. The device as claimed in claim 2, wherein said support and positioning means comprise a solid partition with substantially parallel faces, which is integral with said support, and wherein the housing means consist of an opening made in said solid partition, said opening having a contour which substantially matches the shape of that of said at least one filter.

4. The device as claimed in claim 2, wherein said housing means comprises an insert of stirrup shape which is constructed and arranged to receive said at least one filter and which has an internal surface of a contour substantially matching the shape of that of said at least one filter, and wherein means are provided for removable mounting of the insert in the support.

5. The device as claimed in claim 1, wherein said support and positioning means comprise a solid partition with substantially parallel faces, which is integral with said support, and wherein the housing means consist of an opening made in said partition, said opening 8 having a contour which substantially matches the shape of that of said at least one filter.

6. The device as claimed in claim 1, wherein said housing means comprise an insert of stirrup shape which is constructed and arranged to receive said at least one filter and which has a internal surface of a contour substantially matching the shape of that of said at least one filter, and wherein means are provided for removable mounting of the insert in the support.

7. The device as claimed in claim 1, wherein said support has an elongate shape, having a relatively large dimension and a relatively small dimension perpendicular to said relatively large dimension and wherein said partition extends along said relatively small dimension.

8. The device as claimed in claim 1, wherein said two compartments contain walls and each of said two compartments is shaped and dimensioned so that a single bag or set of bags of said plurality of bags arranged in said compartment is in contact with all of the walls of said two compartments.

9. The device as claimed in claim 1 wherein said filters are held in said supporting and positioning means by engagement with said bags.

* * * * *